United States Patent [19]

Jay et al.

[11] Patent Number: 5,019,370

[45] Date of Patent: May 28, 1991

[54] BIODEGRADABLE, LOW BIOLOGICAL TOXICITY RADIOGRAPHIC CONTRAST MEDIUM AND METHOD OF X-RAY IMAGING

[75] Inventors: Michael J. Jay; U. Yun Ryo, both of Lexington, Ky.

[73] Assignee: University of Kentucky Research Foundation, Lexington, Ky.

[21] Appl. No.: 377,396

[22] Filed: Jul. 10, 1989

[51] Int. Cl.$^5$ .................... A61K 49/04; A61K 9/14; A61B 5/00
[52] U.S. Cl. ........................... 424/4; 424/5; 424/486; 424/487; 514/951; 128/632
[58] Field of Search ................ 424/4, 5, 486, 487; 514/951, 963; 128/654

[56] References Cited

U.S. PATENT DOCUMENTS

| | | | |
|---|---|---|---|
| 1,858,142 | 5/1932 | Ellzey | 424/5 |
| 1,984,404 | 12/1934 | Ellzey | 424/5 |
| 4,406,878 | 9/1983 | DeBoer | 424/5 |
| 4,680,171 | 7/1987 | Shell | 424/5 |
| 4,783,484 | 11/1988 | Violante et al. | 514/535 |
| 4,804,529 | 2/1989 | Bardy et al. | 424/9 |

FOREIGN PATENT DOCUMENTS 400935  7/1975  United Kingdom .

OTHER PUBLICATIONS

Kreuter, J. 1983, Pharm. Acta Helv. 58(7); 196–209, Evaluation of Nanoparticles as Drug-delivery Systems, I. Preparation Methods.
"Radiographic Contrast Agents", R. E . Miller, M.D. and J. Skucas, M.D., University Park Press.
"Particulate Contrast Media", M. R. Violante et al.
"Computed Tomographic Enhancement of Liver and Spleen in the Dog with Idipamide Ethyl Ester Particulate Suspensions", Violante and Gadeholt.
"Effect of Intraveneously Administered Iodipamide Ethyl Ester Particles on Rat Liver Morphology", Lauteala et al.

*Primary Examiner*—Stanley J. Friedman
*Assistant Examiner*—Terry L. Wilson
*Attorney, Agent, or Firm*—Lowe, Price, LeBlanc & Becker

[57] ABSTRACT

A biodegradable, low biological toxicity, particulate radiographic contrast medium comprises biodegradable polymeric spheres of average molecular weight average diameter about 10–1,000 nm or about 0.01–1.0 micron carrying in at least radiographic contrasting amount of a radiographically opaque element.

A method of obtaining a tomographic image of the body portion of a subject comprises administering to the subject a radiographically-detectable amount of the biodegradable, low-toxicity radiographic medium of claim 1; allowing for the spheres to be taken-up by the body portion; and X-raying an area comprising the body portion.

A method of improving the contrast of a tomographic image of a body portion of a subject comprises administering to the subject a radiographically-detectable amount of the biodegradable, low-toxicity radiographic medium of claim 1; allowing for the spheres to be selectively taken-up by the body portion; and X-raying an area comprising the body portion.

19 Claims, No Drawings

BIODEGRADABLE, LOW BIOLOGICAL TOXICITY RADIOGRAPHIC CONTRAST MEDIUM AND METHOD OF X-RAY IMAGING

TECHNICAL FIELD

This invention relates to a new radiographic contrast medium for computerized tomographic (CT) imaging of portions of the subject's body. The medium disclosed herein provides a polymer comprising a specified particulate size compounds previously used as water-soluble contrast agents. The polymers are designed so that they precipitate into particles of a specific size which can be taken up by organs such as the liver or spleen. In addition, the present medium can also be utilized as a vascular contrast agent due to its extensive retention in the blood vessels.

BACKGROUND ART

The field of medical radiography is well known. This is an extremely valuable tool for the early detection and diagnosis of various diseases of the human body. Different parts of the human body such as cavities and soft tissues of various organs and blood vessels evidence low X-ray radiation absorption. Thus, radiographing these body portions is difficult. To overcome this hurdle contrast agents which are opaque to X-ray radiation have been used.

Several inorganic materials have been used as contrast agents. Examples of these are bismuth subnitrate, bismuth subcarbonate, and barium sulfate, among others. U.S. Pat. No. 4,709,703 discloses a method of imaging an organ's tissue by perfusion with beads made of a metal or tungsten of 15–18 micron diameter.

Iodinated organic agents have also been used as contrast agents since the iodine atom is an effective X-ray absorber. Among these are iodinated oils, such as ethyl iodo-phenylundecylate, used for myelography, and water-soluble, iodinated organic compounds used for X-ray visualization of the gastrointestinal tract.

Water-soluble, iodinated organic compounds, however, can cause extremely severe side effects when used as a gastrointestinal contrast agent in dehydrated patients, especially infants. For this reason, these materials have become quite controversial and some radiologists no longer use such agents in the gastrointestinal tract (See, Radiographic Contrast Agents, Miller et al, p 169, University Park Press, Baltimore, Md. 21202 (1977)).

Water-insoluble, iodinated organic polymers have been used as contrast agents, as well. Such is the case of the product disclosed in British Patent Specification No. 1,400,985. This patent describes polymers containing iodine-substituted aromatic groups which are readily swellable in water to yield a gel. The iodine content of the polymers is between 20 and 35 wt %.

Biodegradable microspheres labeled with X-ray absorbent material have been used as contrast agents for the visualization of arterial circulation and the diagnosis of pulmonary embolism and other diseases in humans. U.S. Pat. No. 4,680,171 provides a method of visualizing the arterial circulation of a person by administering microspheres bearing an X-ray absorbent material, and subsequently X-raying the area of arterial circulation sought to be visualized. The medium utilized in this patent has microspheres of a 9–100 micron diameter. Examples of materials utilized in the prior art patent are albumin and starch.

U.S. Pat. No. 4,406,878 discloses a method for forming radiographic images of a body portion such as a human organ by introducing into the body portion a water-insoluble, non-water swellable iodinated polymer having an iodine content in excess of 35 wt % and then X-ray imaging the organ. The polymer is composed of a repeating organic unit forming the backbone chain of the polymer, and iodinated aromatic groups and hydrophilic groups which stick out from the backbone chain. The diameter of the polymer beads can be as high as 1,000 microns. The hydrophilic groups containing the iodine are attached to the backbone of the polymer by a linking group which may be an ester, ether, amide, thioester, carbonate, carbamate, sulfide and the like. The particle size of the beads may vary over a very broad range. The medium is therefore very inefficient and expensive to use since large amounts are required for a small proportion of the beads to reach a particular target tissue.

Iodinated compounds have been used in colloidal form in cholecystography. U.S. Pat. No. 1,858,142 discloses the production of a mono- and di-alkali metal salt of tetraiodophenolphthalein in colloidal form. U.S. Pat. No. 1,984,404 describes a similar composition comprising an alkali-metal salt of tetraiodophenolphthalein. The compound is provided for oral administration for the imaging of the hapatobiliary tract.

Water-soluble contrast agents have drawbacks such as their inherent hyperosmolality. Non-ionic agents were developed as a means to reduce hyperosmolality since they have about half the osmolality of their corresponding ionic monomers.

Particulate contrast agents were also developed because the particles make almost no contribution to the osmotic pressure of a medium. Accordingly, the use of particulate contrast agents affords the possibility of administering high iodine content materials which lack the fluid and ion shifts associated with water-soluble agents. An additional advantage of particulate contrast agents is the fact that their increased molecular size has no significant affect on the distribution volume thereof. That means that in fact there is more of the X-ray opaque component retained in the same volume. Moreover, the particulate contrast agents are initially retained exclusively within the vascular space. Only if they are of the correct size will they be phagocytized into the cellular space of an organ. Thus, for an initial period after their administration particulate contrast agents are useful for conducting blood flow and volume studies without using radioisotopes or any complex compartmental analysis necessary to account for any exodus of the particle into interstitial spaces.

Violante et al, Invest. Radiol. 15(6):S329–S334 (November–December 1980), Korman et al, Invest. Radiol. 19:133 (1984), and Sands et al (Invest. Radiol. 22(5):408–416 (May 1987) disclosed particulate contrast agents having diameters in the range of two microns and smaller. The agents are iodinated aromatic structures which are esterified and amidized with methanol and ethanol such as ethyl esters of iothalamic and iodipamic acid. These compounds are preincubated in human serum albumin to overcome in vivo particle aggregation and embolization. Similar compounds are used as antimicrobial agents in particulate form (see, U.S. Pat. No. 4,783,484).

However, the development of suitable particulate contrast agents has not been forthcoming because of the difficulties involved in their development. The size and shape of the particles must be such that they do not cause embolism in the capillaries, and in vivo particle aggregation must be avoided to prevent the occurrence of embolism. The uptake of the contrast agent by the desired tissue must be maximized while at the same time permitting its quick removal within a reasonable period of time. Moreover, any contrast agent to be useful and obtain approval for use in humans must have substantially reduced biological toxicity.

Accordingly, there still is a need for an improved X-ray imaging agent having the above characteristics.

DISCLOSURE OF THE INVENTION

This invention relates to a biodegradable, low biological toxicity, particulate radiographic contrast medium which comprises
    biodegradable polymeric spheres of estimated average molecular weight about $10^5$ to $10^7$ daltons and average diameter about 10-1000 nanometers or about 0.01-1.0 micron and carrying an at least radiographic contrasting amount of a radiographically opaque element.

Also disclosed herein is an imaging composition, which comprises
    a radiographically-detectable amount of the contrast medium of this invention; and
    a pharmaceutically-acceptable, substantially X-ray transparent carrier.

This invention also relates to a method of obtaining a tomographic image of a body portion of a subject, which comprises
    administering to the subject a radiographically-detectable amount of the biodegradable, low-toxicity radiographic medium of this invention;
    allowing for the spheres to be taken-up by the body portion; and
    X-ray imaging an area comprising the body portion.

Still part of the invention is another method of improving the contrast of a tomographic image of a body portion of the subject which comprises
    administering to the subject a radiographically-detectable amount of the biodegradable, low-toxicity radiographic medium of this invention;
    allowing for the spheres to be selectively taken-up by the body portion; and
    X-ray imaging an area comprising the body portion.

A more complete appreciation of the invention and many of the attendant advantages thereof will be readily perceived as the same becomes better understood by reference to the following detailed description when considered in connection with the description of the best mode for carrying out the invention and the examples. Other objects advantages and features of the present invention will become apparent to those skilled in the art from the following discussion.

BEST MODE FOR CARRYING OUT THE INVENTION

This invention arose from the desire of the inventors to improve on prior art products suitable for use as radiographic contrast agents for imaging specific areas of the animal body.

Computerized tomography (CT or CAT) scanning is an imaging technique which utilizes X-rays to produce tomographic images of the body's internal structures. Contrast agents used for this purpose must be capable of attenuating X-rays. Contrast agents which are extremely useful are those which are designed to be taken up preferentially by a portion of the body which is desired to be imaged by means of X-ray technology. This lowers the background noise and permits to obtain better contrast picture of the body portion.

The present invention provides a biodegradable, low biological toxicity, particulate radiographic contrast medium which comprises biodegradable polymeric spheres of estimated average molecular weight about $10^4$ to $10^8$ daltons and average diameter about 10-1,000 nanometers or about 0.01-1.0 micron and carrying an at least radiographic contrasting amount of a radiographically opaque element.

In a preferred embodiment of the invention, the biodegradable polymeric spheres of the invention have an average molecular weight of about $10^5$ to $10^7$ daltons, and still more preferably about 50,000 to 200,000 daltons. In another preferred embodiment the average diameter of the spheres is about 10-900 nanometers or about 0.1-0.9 microns, more preferably about 10 to 800 nanometers or about 0.01-0.8 micron, and still more preferably about 10-500 nanometers or about 0.01-0.5 microns.

In the most preferred embodiment of the contrast medium, the average diameter of the spheres is about 50-500 nanometers or 0.05-0.1 micron, and more preferably about 100-200 nanometers or 0.1-0.2 micron.

The present contrast medium is particularly suited for imaging of the vascular regions of the body as well as organs such as the liver and spleen because of the specific range of the diameter of the spheres. Because of the diameter range of the polymeric spheres the present contrast medium may be phagocytized by, e.g., the Kupffer cells of the liver and by the spleen. Since the present contrast medium comprises particulate material it, in fact, delivers a higher content of the radiographically opaque element than the corresponding soluble or non-polymeric materials.

The present contrast medium is especially well suited for enhancement of liver and spleen images because it is substantially not eliminated through the kidneys. Thus, it can be effectively used in renal failure patients. One of the drawbacks of water-soluble contrast media is that, in renal failure patients, toxic levels of the agent may build up in the body. The present contrast media can thus be safely used in this large group of patients, i.e., renal failure patients.

In another preferred embodiment, the polymeric spheres may be loaded with the radiographically opaque element in order to optimize the utilization of the agent. That is, the higher the radiographically opaque element content of the spheres the lesser the amount of contrast medium necessary to obtain a suitable X-ray image of a body portion and the higher the contrast of the resulting picture.

The particles of the present medium are biodegradable which means that they can be chopped up into smaller molecules and excreted from the body within a suitable period of time after administration. Typically, the polymeric spheres are at least partially hydrolyzed by enzymes which occur in the body prior to excretion. Examples of these enzymes are esterases, amidases, proteases, pseudocholinesterase, lysozyme, elastase and collagenase. In addition, some of the polymers are also hydrolyzable at different pHs encountered in the body. Because they are biodegradable the polymeric spheres are not retained for extended time periods in the organs into which they are taken up.

Moreover, the present contrast medium is substantially non-biologically toxic, and can, therefore, be administered in amounts as large as needed, including to humans.

In one preferred embodiment the contrast medium of the invention comprises a polymer which is selected from the group consisting of polyesters, polyamides, polycarbonates, polycarbamates, and polyureas, derivatives thereof, analogues thereof and pharmaceutically-acceptable salts thereof.

Typical polyesters are succinates, acrylates, esters of ($C_2$-$C_{20}$)alkyl mono- and di-acids with ($C_2$-$C_{30}$)alkyl, alkenyl, alkynyl or ($C_6$-$C_{30}$)aryl hydroxylated compounds, derivatives thereof, analogues thereof and co-polymers thereof with other monomers. Preferably, the hydroxylated compounds and/or the other monomers have covalently attached thereto the radiographically opaque element(s).

Examples of polyamides are acrylamides, ($C_2$-$C_{30}$)alkyl, alkenyl or alkynyl acrylamides, amides of ($C_2$-$C_{30}$)alkyl, alkenyl or alkynyl mono- or di-acids or ($C_8$-$C_{30}$)aryl mono- and di-acids with ($C_2$-$C_{30}$)alkyl, alkenyl or alkynyl or ($C_6$-$C_{30}$)aryl aminated compounds, derivatives thereof, analogs thereof and co-polymers thereof with other monomers. Preferably, the aminated compounds and/or the monomers have bound thereto the radiographically opaque element(s).

The derivatives may comprise, in addition, substituents such as halogen, ($C_1$-$C_8$)alkyl, alkenyl or arometic or heterocyclic. However, other derivatives which do not interfere with the activity of the spheres in a negative fashion may also be utilized.

The analogues may have a similar chemical formula but different conformation, substitutions of one monomer, acid, or hydroxylated or aminated compound for another, and the like.

In another preferred embodiment of the invention the radiographically opaque element may be added to the polymeric spheres after they have been formed. This can be attained by methods known in the art. (Mayberry, W. E., and Hockert, T. J., "Kinetics of Iodination", J. Biol. Chem. 245: 697–700 (1970); Thorell, J. I. and Johensson, B. G., "Enzymatic Iodination of Polypeptides with I-125 to High Specific Activity", Biochem. Biophys. Acta. 251:363–369 (1971)).

The mono- and di-acids, the hydroxylated compounds, the aminated compounds and the monomers utilized for the manufacture of the present biodegradable polymeric spheres are prepared by methods known in the art which need not be repeated herein. (Krewter, J. "Evaluation at Nanoparticles as Drug-Delivery Systems. I: Preparation Methods", Pharm. Acta. Helv. 58:196–209 (1983)).

The co-polymers encompass typically, co-polymers with monomers such as tetraciodophenolphthalein, iocetamic acid, iodoalphionic acid, iopanoic acid, iophenoxic acid, and ipodate. However, other monomers known to be pharmaceutically acceptable and substantially biologically non-toxic are also suitable.

A particularly preferred polyester is that which is formed from an acrylate and/or succinate, analogues thereof or derivatives thereof with an hydroxylated compound. Also suitable are esters of malonate, maleate, and/or glutarate. However, other types of esters may also be utilized within the confines of this invention.

A particularly preferred polyamide is one formed from tetraiodophenolpthalein, iopanoic acid, iodoalphionic acid, and/or iocetamic acid, analogues thereof and derivatives thereof with an aminated compound.

Preferred hydroxylated compounds are lactate, hydroxybutyrate, and hydroxyvalerate. However, others may also be utilized. Derivatives thereof, particularly active derivatives reacting with carboxyl groups, may also be utilized. Examples are epoxides, and the like.

Preferred aminated compounds are glycine and sarcosine. However, others are also suitable. Active derivatives thereof are also useful such as aziridines and the like.

The biodegradable, low biological toxicity, particulate radiographic contrast medium of the invention, may further comprise
an additive selected from the group consisting of colorants, preservatives, stability enhancing agents, biological transport enhancing agents, suspending agents, osmotic agents, salts and the like.

Examples of colorants are any FDA approved dyes. Examples of preservatives are benzoic acid and the like. Examples of stability enhancing agents are povidone and polyvinyl alcohol. Examples of biological transport enhancing agents are povidone and the like. Examples of suspending agents are dextran and dextrose. However, other colorants, preservatives, stability enhancing agents, biological transport enhancing agents, suspending agents, osmotic agents and salts may also be utilized as is known in the art. All these additives are added in amounts known in the art and are prepared by methods also known in the art.

The radiographically opaque element utilized for the practice of this invention may be selected from the group consisting of iodine, bromine, samarium, erbium, and other lanthanides. These are known in the art as are the methods for incorporating them into monomeric and polymeric organic molecules. (Ber 28:1603 (1895) Classen a Lok; Morgan, P. W., "Linear Condensation Polymers from Phenolphthalein and Related Compounds" J. Polymer Sc. 2:437–459 (1964)).

In a most preferred embodiment of the invention the radiographically opaque element is iodine.

In another preferred aspect of the invention the radiographically opaque element is covalently bound to the polymer. However, it may also be loaded into the polymeric spheres by methods known in the art. (Mayberry, W. E. and Hockert, T. J., "Kinetics of Iodination", J. Biol. Chem. 245: 697–700 (1970); Thorell, J. I. and Johensson, B. G., "Enzymatic Iodination of Polypeptides with I-125 to High Specific Activity", Biochem. Biophys, Acta. 251:363–369 (1971)).

Typically, the radiographically opaque element is present in the polymeric spheres in an amount of about 10 to 90 wt % of the polymer, more preferably about 30 to 75 wt %, and still more preferably about 40 to 60 wt %.

The radiographic contrast medium of the invention may also be provided as an imaging composition, comprising
a radiographically-detectable amount of the contrast medium of the invention; and
a pharmaceutically-acceptable substantially X-ray transparent carrier.

The radiographic contrast agent of the invention may be provided either in a dry or liquid state, depending on the type of carrier added to the polymer. For example, in the dry state the polymeric spheres may be compounded with a dry binder and provided for instance in tablet or powder form. In the liquid state, which is a preferred state of the present radiographic contrast medium for introduction into the body of the test subject, the polymeric spheres are suspended in an aqueous liquid carrier as particulate, water-insoluble, nonwater-swellable beads.

Examples of solid carriers are lactose, povidone, and the like. Examples of liquid carriers are solutions of normal saline and 5% dextrose in water. However, others may also be utilized herein.

In another embodiment of the invention, the radiographic contrast medium is provided as a surgical element comprising a surgical substrate as a carrier, e.g., a surgical instrument, dressing, suture or implant carrying a radiographically effective amount of the radiographic contrast medium. The manner in which these may be applied to the body is known in the art and need not be further described herein. The amounts of radiographic contrast medium delivered to the body are similar to those provided either orally or systemically.

In a preferred embodiment of the invention the radiographic contrast medium consists essentially of the biodegradable polymeric spheres carrying the radiographically opaque element.

Also part of this invention is a method of obtaining a tomographic image of a body portion of a subject, which comprises
- administering to the subject a radiographically-detectable amount of the biodegradable, low-toxicity radiographic medium of this invention;
- allowing for the spheres to be taken-up by the body portion; and
- X-ray imaging an area comprising the body portion.

The administration of the radiographic contrast medium is conducted by methods known in the art. Preferred is intravenous administration but the medium may be administered by other routes. Examples are oral, intraarterial and intracatheter routes. Other routes of administration are also possible, such as subcutaneous administration. Typically, the contrast medium of the invention is administered in an amount of about 1 to 500 milligrams/kg of body weight and more preferably about 10 to 20 milligrams/kg of body weight. However, other amounts may also be utilized.

After the administration of the contrast agent there is a waiting period so that the polymeric spheres may be taken-up by the target body portion desired to be imaged. This period may extend for about 2 to 60 minutes, and in some instances for up to 4 hours. However, this waiting period depends on the characteristics of the particular polymeric material contained in the contrast agent. An artisan would know based on the characteristics of the polymer how to dose each individual type of polymer encompassed by this invention.

The X-ray imaging step may be conducted by well known techniques and utilizing commercially available X-ray apparatuses. The visualization of the thus obtained X-ray image may be conducted also by well-known techniques including the use of a conventional X-ray sensitive phosphor screen-silver halide photographic film combination, various electrophotographic techniques such as xeroradiography and other radiographic visualization techniques such as computerized axial tomography (CAT or CT) and ionographic techniques.

Preferred is the X-raying by computerized axial tomography or CAT.

Typically, in the period immediately following the administration of the contrast agent the vascular areas of the body may be visualized. Thereafter, particularly after 10 minutes the polymeric spheres start to be taken up by specific organs such as the liver and/or the spleen and may be utilized for the imaging of these areas. This is of particular importance and utility in cases of renal failure when the retention in these organs of the contrast agent is prolonged.

Also provided herein is a method of improving the contrast of a tomographic image of a body portion of a subject, which comprises
- administering to the subject a radiographically-detectable amount of the biodegradable, low toxicity radiographic medium of this invention; described above or a composition comprising it;
- allowing for the spheres to be selectively taken-up by the body portion; and
- X-ray imaging an area comprising the body portion.

In general, these steps may be conducted as described above. Because of their particular molecular weight and diameter, the spheres are selectively taken-up by organs such as the liver and spleen. The medium or imaging composition of the invention can also be utilized for the visualization, in the period immediately following administration thereof, of the vascular portions of the body. In addition, because the spheres are substantially not eliminated by the kidneys, they are safe to use in renal failure patients.

Having now generally described this invention, the same will be better understood by reference to certain specific examples, which are included herein for purposes of illustration only and are not intended to be limiting of the invention or any embodiment thereof, unless so specified.

EXAMPLES

Example 1: Intravenous Contrast Agent

The present agent is a new reticuloendothelial-specific intravenous contrast agent for enhancement of liver and spleen at CT scanning. A polyester of tetraiodophenolphthalein (TIP) was prepared by reacting a solution of sodium TIP in 0.1 M borate buffer containing various quantities of dextran with succinyl chloride dissolved in dichloroethane. The succinyl chloride solution is added dropwise to the stirred TIP solution and the emulsion polymerization reaction is allowed to continue until the blue color in the TIP solution has completely disappeared and given way to an off white suspension. The dichloroethane is removed under reduced pressure and the resultant product is gently centrifuged for 15 min (and washed twice in a similar manner) to remove large aggregrates. The resulting suspension is then centrifuged at high speed and the sedimented nanoparticles are washed twice with water. A portion of the nanoparticles are dried under vacuum for determination of yield. The nanoparticles are then suspended in 5% dextrose in water (D5W) prior to administration. The polyester of TIP is about 58% iodine by weight and precipitates as a monodisperse suspension with a mean particle diameter of 200 nm.

Example 2: CT Imagining with Agent

CT images of a group of rabbits injected with the agent demonstrated marked and selective enhancement of liver and spleen (greater than 100 HU), which gradually declined over a period of 2–3 weeks.

No evidence of renal concentration or elimination was encountered.

Example 3: Determination of Other Effects

Serial blood samples obtained for some 16 days following the administration of contrast agent revealed no abnormalities in liver enzymes, or in bilirubin, BUN, creatinine or electrolytes.

Radiolabeled TIP polymer confirmed the selective accumulation of the agent in the liver and spleen, with less than 1% in the bone marrow.

Radioactive tracer followed in feces indicated biliary elimination of the agent.

No radioactivity was recovered in the urine.

This polymer is expected to undergo biodegradation upon hydrolysis of its ester linkages to TIP, a previously used contrast medium of low toxicity.

The invention now being fully described, it will be apparent to one of ordinary skill in the art that many changes and modifications can be made thereto without departing from the spirit or scope of the invention as said forth herein.

We claim:

1. A biodegradable, low biological toxicity, particulate radiographic contrast medium, comprising
   biodegradable polymeric spheres of estimated average molecular weight about $10^5$ to $10^7$ daltons, average diameter about 10–1,000 nm or about 0.01–1.0 micron, said spheres carrying an at least radiographic contrasting amount of a radiographically opaque element and said polymeric spheres have a polymer backbone made up of polymerized monomer radiographically opaque units or said polymeric spheres are a copolymer which has a backbone of monomer radiographically opaque units and other monomers that is copolymerized.

2. The radiographic contrast medium of claim 24, wherein
   the polymer is selected from the group consisting of polyesters, polyamides, polycarbonates, polycarbamates and polyureas, derivatives thereof, analogues thereof, co-polymers thereof with other monomers and pharmaceutically acceptable salts thereof.

3. The biodegradable, low biological toxicity, particulate radiographic contrast medium of claim 2, wherein
   the polymer is a polyester.

4. The biodegradable, low biological toxicity, particulate radiographic contrast medium of claim 3, wherein
   the polyester is a succinate or acrylate ester of a $(C_2-C_{30})$alkyl, alkenyl or alkynyl mono- or di-acid, or a $(C_8-C_{30})$aryl mono- or di-acid with a $(C_2-C_{30})$alkyl, alkenyl or alkynyl or a $(C_6-C_{30})$aryl hydroxylated compound, derivatives thereof, analogues thereof or co-polymers thereof.

5. The biodegradable, low biological toxicity, particulate radiographic contrast medium of claim 2, wherein
   the polymer is a polyamide.

6. The biodegradable, low biological toxicity, particulate radiographic contrast medium of claim 5, wherein
   the polyamide is a polyamide of a $(C_2-C_{30})$alkyl, alkenyl or alkynyl mono- or di-acid or a $(C_8-C_{30})$aryl mono- or di-acid with a $(C_2-C_{30})$alkyl, alkenyl or alkynyl or a $(C_6-C_{30})$aryl aminated compound, derivatives thereof, analogues thereof or co-polymers thereof.

7. The biodegradable, low biological toxicity, particulate radiographic contrast medium of claim 24, wherein
   the average diameter of the spheres is about 50–500 nanometers.

8. The biodegradable, low biological toxicity, particulate radiographic contrast medium of claim 7, wherein
   the average diameter of the spheres is about 100 to 200 nanometers.

9. The biodegradable, low biological toxicity, particulate radiographic contrast medium of claim 24, further comprising
   an additive selected from the group consisting of colorants, preservatives, stability enhancing agents, biological transport enhancing agents, suspending agents, osmotic agents and salts.

10. The biodegradable, low biological toxicity, particulate radiographic contrast medium of claim 24, wherein
    the radiographically opaque element is selected from the group consisting of iodine, bromine and lanthanides.

11. The biodegradable, low biological toxicity, particulate radiographic contrast medium of claim 10, wherein
    the radiographically opaque element is iodine.

12. The biodegradable, low biological toxicity, particulate radiographic contrast medium of claim 24, wherein
    the radiographically opaque element is covalently bound to the polymer.

13. The biodegradable, low biological toxicity, particulate radiographic contrast medium of claim 24, wherein
    the radiographically opaque element is present in an amount of about 40 to 90 wt % of the polymer.

14. The biodegradable, low biological toxicity, particulate radiographic contrast medium of claim 24, consisting essentially of
    the biodegradable polymeric spheres.

15. An imaging composition, comprising
    a radiographically-detectable amount of the contrast medium of claim 24; and
    a carrier.

16. The imaging composition of claim 15, comprising about 1 to 20 wt % of biodgradable polymeric spheres.

17. The biodegradable, low biological toxicity, particulate radiographic contrast medium of claim 3, wherein
    the polyester is derived from tetraiodophenolphthalein, analogs thereof or copolymers thereof.

18. The biodegradable, low biological toxicity, particulate radiographic contrast medium of claim 5, wherein
    the polyamide is a polyamide of tetraiodophenolphthalein derivative, analogs thereof or copolymers thereof.

19. The biodegradable, low biological toxicity, particulate radiographic contrast medium of claim 10, wherein
    the radiographically opaque element is iodine in a tetraiodophenolphthalein derivative.

* * * * *